United States Patent
Rantala (10) Patent No.: US 7,029,447 B2
(45) Date of Patent: Apr. 18, 2006

(54) MEASURING BLOOD PRESSURE

(75) Inventor: Börje Rantala, Helsinki (FI)

(73) Assignee: Instrumentarium Corporation, Helsinki (FI)

( * ) Notice: Subject to any disclaimer, the term of this patent is extended or adjusted under 35 U.S.C. 154(b) by 250 days.

(21) Appl. No.: 10/635,315

(22) Filed: Aug. 6, 2003

(65) Prior Publication Data

US 2004/0030261 A1    Feb. 12, 2004

(30) Foreign Application Priority Data

Aug. 9, 2002    (EP)    ................... 02396121

(51) Int. Cl.
*A61B 5/02* (2006.01)
(52) U.S. Cl. ................ 600/485; 600/509; 600/547
(58) Field of Classification Search ............... None
See application file for complete search history.

(56) References Cited

U.S. PATENT DOCUMENTS

| | | | |
|---|---|---|---|
| 4,807,638 A | | 2/1989 | Sramek |
| 5,101,825 A | * | 4/1992 | Gravenstein et al. ....... 600/326 |
| 5,309,916 A | | 5/1994 | Hatschek |
| 5,490,523 A | * | 2/1996 | Isaacson et al. ............ 600/323 |
| 5,782,756 A | * | 7/1998 | Mannheimer ............... 600/322 |
| 6,648,828 B1 | * | 11/2003 | Friedman et al. ........... 600/506 |

FOREIGN PATENT DOCUMENTS

| | | |
|---|---|---|
| DE | 100 61 189 | 6/2002 |
| EP | 0 852 126 | 7/1998 |
| EP | 1 078 597 | 2/2001 |
| WO | 96/11625 | 4/1996 |

* cited by examiner

*Primary Examiner*—Robert L. Nasser
*Assistant Examiner*—Patricia C Mallari
(74) *Attorney, Agent, or Firm*—Andrus, Sceales, Starke & Sawall, LLP (57) ABSTRACT

The present invention concerns a method and a system for measuring non-invasively a blood pressure of a patient. The method comprises the steps of: determining (1603) a mechanical heart beat starting time point from an impedance cardiogram signal, detecting (1605) a heart beat pulse arrival time at a peripheral site of the patient, calculating (1607) a pulse wave transit time from the heart to the peripheral site by utilizing said mechanical starting point of the heart beat and said heart beat pulse arrival time, calculating (1609) an estimate of the blood pressure of the patient from said pulse wave transit time.

10 Claims, 13 Drawing Sheets

MEASURING BLOOD PRESSURE

CROSS REFERENCE TO RELATED APPLICATION

The present application claims priority from European Patent Application No. 02396121.2, filed Aug. 9, 2002.

FIELD OF THE INVENTION

The present invention relates to blood pressure monitoring systems. In particular, the present invention relates to a novel and improved method and system for non-invasive blood pressure measurement.

BACKGROUND OF THE INVENTION

Non-invasive blood pressure measurement is often done by measuring the pulse wave transit time from the heart to the finger. Namely the pulse wave transit time and thus the pulse wave velocity are dependent on the blood pressure. Also, changes in blood pressure can be measured by measuring changes in pulse wave transit time or pulse wave velocity (PWV). The prior art methods are measuring PWV continously from the electrocardiogram (ECG) r-wave to the pulse oximeter plethysmogram wave crest. These measurements require calibrating the value with a standard non-invasive blood pressure cuff reading. A typical measurement method of this kind is oscillometric cuff measurement.

Another prior art measurement method is a standard finger oximetry pleth measurement.

The prior art measurement principles have problems at both ends; the delay from the heart electrical-to-mechanical activity is variable and not easily controllable, and the standard finger site for oximetry pleth is very sensitive to vasoconstriction, that affects the hand, i.e. palm and finger, pulse delays in a highly variable manner. Often, as with sick patients with low peripheral perfusion, the finger pulse is not detectable at all or very noisy.

The heart side of the measurement problem has in prior art been solved by adding an ear plethysmographic probe, and monitoring the ear-finger pulse transit time; the obvious drawback is the extra sensor needed. In practical clinical conditions the extra sensor is difficult to use.

Circulation and Blood Pressure

In this invention, three physiological signals originating from the circulatory system are measured to produce continuous information on blood pressure changes: the electrocardiogram, the impedance cardiogram, and the photoplethysmogram arising from a pressure pulse passing through a vessel. In addition, an intermittent blood pressure measurement method is used for repetitive calibration.

Circulatory System

Figure 1:
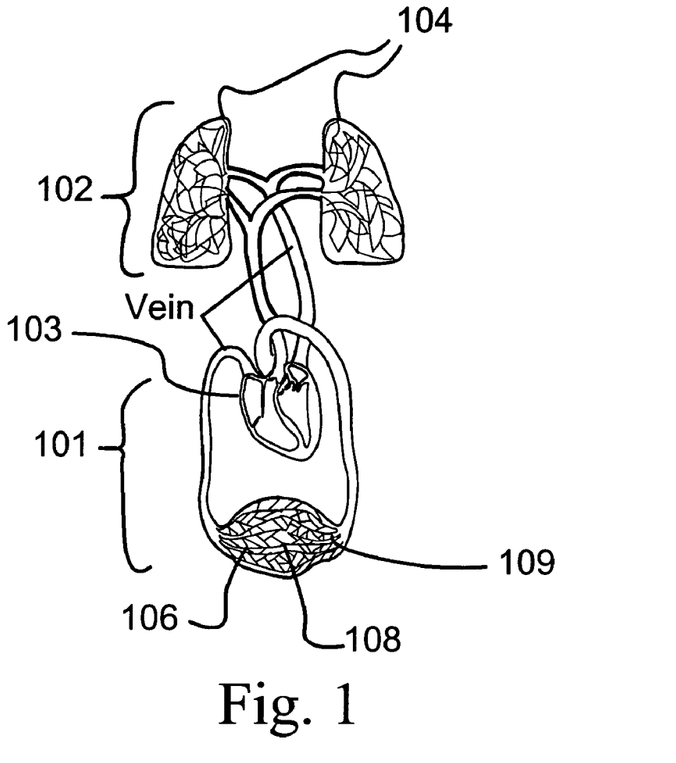
FIG. 1 shows the circulatory system of a person.

FIG. 1 shows the circulatory system of a person. The system consists of both the systemic 101 and the pulmonary 102 circulation. The circulatory system of a person or patient also consists also of the heart 103. The pulmonary circulation 102 supplies the lungs 104 with blood flow, while the systemic circulation takes care of all the other parts of the body i.e. the systemic circulation 101. The heart 103 serves as a pump that keeps up the circulation of the blood. The systemic circulation consist of the venule 106, the capillary system 108 and the arteriole 109.

Blood Pressure

Blood pressure is defined as the force exerted by the blood against any unit area of the vessel wall. The measurement unit of blood pressure is mmHg. This means millimeters of mercury.

Figure 2:
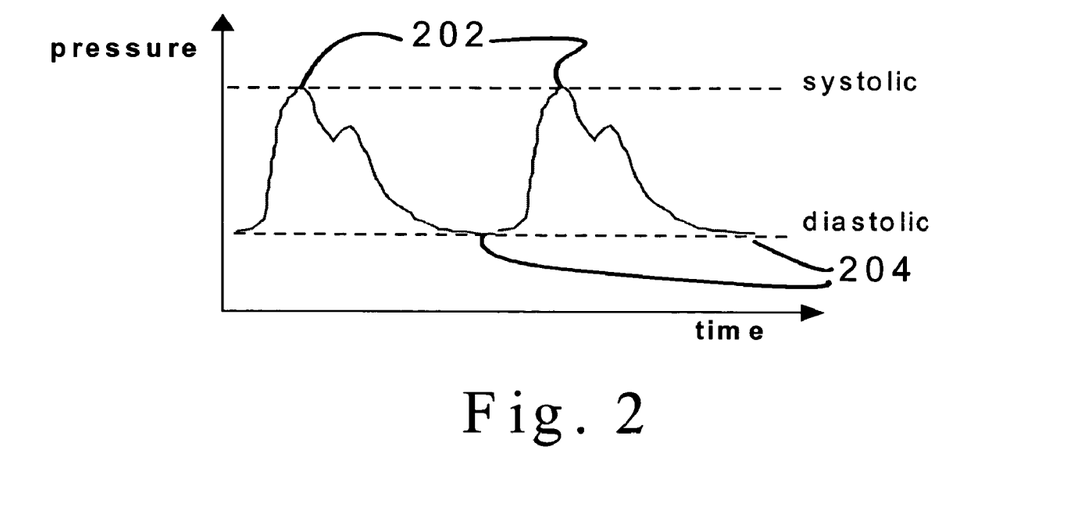
FIG. 2 shows the definition of systolic and diastolic blood pressure values.

FIG. 2 shows the definition of systolic 202 and diastolic 204 blood pressure values. Pulmonary and systemic arterial pressures are pulsatile, having systolic 202 and diastolic 204 values. As illustrated in FIG. 2, the highest recorded pressure reading is called systolic pressure 202. It results when the volume of the heart decreases during contraction, while the volume of blood in the circulation remains constant. The lowest pressure reading is called diastolic pressure 204.

Electrical Activity of the Heart

The pumping action of the heart is a consequence of periodical electrical events occurring in the cardiac muscle tissue. These electrical events can be measured by an electrocardiogram ECG and they are further elaborated in the following in connection with FIG. 3.

Events of the Cardiac Cycle

Figure 3:
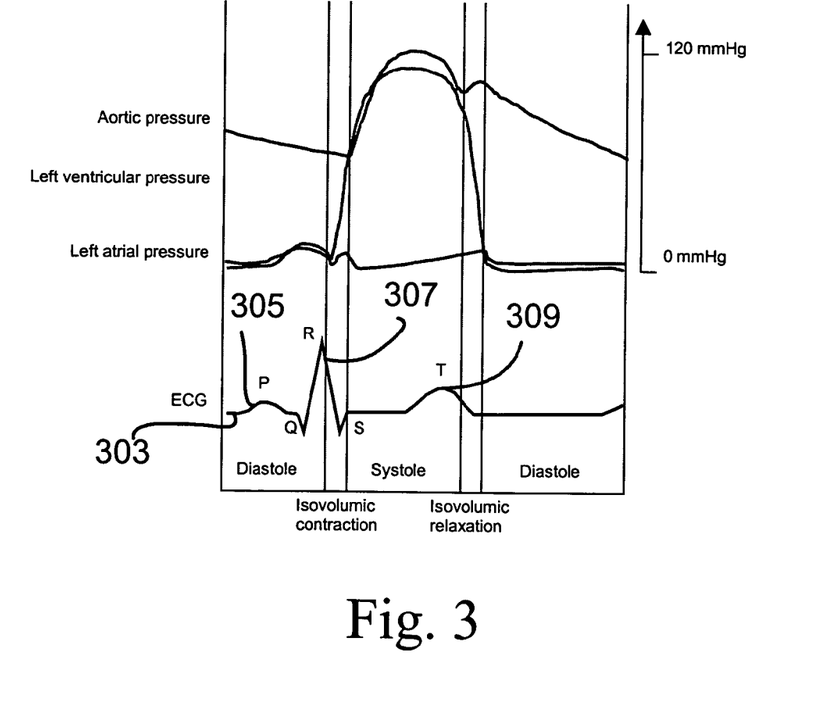
FIG. 3 shows the timing of the electrical and mechanical events of the cardiac cycle.

FIG. 3 shows the timing of the electrical and mechanical events during one cardiac cycle. A cardiac cycle consists of all the events that occur between the beginning of a heartbeat and the beginning of the next heartbeat.

The P wave 305 of the ECG curve 303 is caused by the depolarization of the atria. It is followed by atrial contraction, indicated by a slight rise in the atrial pressure. The QRS wave 307 of the ECG 303 appears as the ventricles depolarise, initiating the contraction of the ventricles.

The repolarisation 309 of the ventricles, indicated by the T wave of the ECG, suddenly causes the ventricles to begin to relax.

Pulse Wave Transit Time Method

Many experiments are reported in which pulse wave velocities or pulse transit times were measured and used to evaluate blood pressure or blood pressure change.

In practice, pulse wave transit times are usually measured rather than velocities. Peripheral pressure pulses are detected by photoplethysmography.

The current opinion is that changes in pulse wave velocity or transit time indeed predict blood pressure changes.

In this text, pulse wave transit time is the time that elapses as a pulse wave propagates from one site to another. It is inversely proportional to the velocity of the pulse wave. A delay is the time between two events. It may include propagation periods and other time lapses.

Measurement Principle

When the left ventricle of the heart contracts and ejects blood into the aorta, only the proximal portion of the aorta becomes distended. The distension then spreads as a wave front along the walls of the arteries and arterioles. The velocity of the pulse wave is 3–5 m/s in the aorta, 7–10 m/s in large arterial branches, and 15–35 m/s in small arteries. In general, the smaller the distensibility of the vessel wall, the faster the pulse wave propagates. The total transit time from the aortic root to the periphery is in the order of 100 ms. FIG. 3 gives an example of four pressure waveforms measured at different sites after the ejection of blood from the heart.

As the pulse propagates towards the periphery, the vessel diameter and the distensibility of the vessel wall decrease, changing the transmission properties and distorting the pulse contour. Most of the distortion is, however, caused by reflected pulse waves that combine with the pulses travelling towards the periphery. The main reflection occurs as the pulse wave reaches the high-resistance peripheral arteries, but arterial lesions or junctions of large arteries can cause additional reflections.

Consider two cardiogenic signals that can be obtained with surface electrodes: the electrocardiogram (ECG) and the impedance cardiogram (ICG). Table 1 summarizes their characteristics and suitability for timing the onset of the pressure pulse.

TABLE 1

Suitability of two different signals for determining the onset time of the pulse wave.

| signal | ECG | ICG |
|---|---|---|
| what is measured | electrical potentials on the surface of the thorax | cardiac related impedance changes by applying current and measuring potentials on the surface of the thorax |
| origin of the signal | electrical activation of the heart | mechanical function of the heart |
| advantages | R waves are readily detectable | indicates the true onset time of the pressure pulse |
| drawbacks | the PEP between the R wave and the onset of the pressure pulse may not be constant | the signal may be noisy and formless, and the actual origin is obscure (thus the question mark) |

Possible Problems

There are numerous physiological factors that influence the pulse wave velocity and/or the pre-ejection period (PEP). Most of these unpredictable mechanisms act on the PEP, not on the actual transit time. Elimination of the contribution of the PEP was thus supposed to improve the technique.

A more likely problem associated with the sympathetic mechanisms is the vasoconstriction of the peripheral arteries, triggered by emotional stress, cold, exercise, or shock. Vasoconstriction changes the peripheral resistance, thus affecting pulse wave transmission and reflection.

Electrocardiography

Electrocardiogram (ECG) is a recording of electrical potentials generated by the function of the heart. The ECG is measured as potential differences between electrodes placed on the surface of the body on standardized positions. This is depicted especially in connection with FIG. 4.

SUMMARY OF THE INVENTION

A target of the invention is to develop a method and a system so that the abovementioned drawbacks of the prior art are circumvented. In particular the target of this invention is to develop a method and a system for measuring blood pressure continuously and non-invasively more accurately than before. A target of the invention is to realize a workable system for measuring pulse wave transit time from the heart to the periphery. The ultimate goal of the invention is to create a method and a system for monitoring blood pressure changes continuously, non-invasively and without excessive equipment.

The target of the invention is achieved by a method and a system that is characterised by those features that are depicted in the independent patent claims.

In particular the target of the invention is achieved by a method that is characterized by the method that comprises the steps of: determining a mechanical heart beat starting time point from an impedance cardiogram signal, detecting a heart beat pulse arrival time at a peripheral site of the patient, calculating a pulse wave transit time from the heart to the peripheral site by utilizing said mechanical starting point of the heart beat and said heart beat pulse arrival time, calculating an estimate of the blood pressure of the patient from said pulse wave transit time.

The invention relates also to a system for measuring non-invasively the blood pressure of a patient.

The target of the invention is achieved by a system that is characterized by that the system comprises: an impedance cardiogram for determining the mechanical heart beat starting time point of a patient, a peripheral site sensor for determining the heart beat pulse arrival time at the peripheral site of the patient, a first calculator for calculating the pulse wave transit time from the heart to the peripheral site by utilizing said mechanical starting point of the heart beat and said heart beat pulse arrival time at the peripheral site of the patient, a second calculator for calculating the blood pressure of the patient from said pulse wave transit time.

To enhance the correlation between measured transit times and blood pressure, impedance cardiography is utilized in pulse wave timing, and a new peripheral measurement site is utilized in the invention. The invention corrects all of the aforementioned problems of the prior art.

Using a wrist plethysmographic sensor, preferably using two unused channels of a four-wavelength oximeter, removes the last part of the transit time error source. As the wrist pleth sensor only needs a pulse waveform, no accuracy or stability requirements are important, and thus a reflective sensor can be employed.

As the pulse wave velocity, i.e. transit time, is correlated to the blood pressure in a very patient specific manner, the relation must be calibrated by a standard oscillometric cuff measurement. The calibration is preferably done incrementally at several different pressure levels, every new reading increasing the accuracy of the calibration. Thus the first cuff reading produces a single point calibration, the result of which only applies close to the pressure level encountered at that time. Watching for pwv variations, these are employed to trigger new cuff inflations, which add calibration points. Alternatively the incremental calibrations can be done by timed cuff inflations.

The invention is based on the inventive idea that using the impedance cardiographic signal as the pulse wave start point removes the electrical-mechanical delay without adding sensors. The peripheral heart beat arrival time is detected and a pulse wave transit time from the heart to the peripheral site is calculated. This calculation is made by using the mechanical starting point of the heart beat and the pulse arrival time of the heart beat at the peripheral site. By utilizing the pulse wave transit time an estimate for the blood pressure of the patient is calculated.

BRIEF DESCRIPTION OF THE DRAWINGS

The accompanying drawings, which are included to provide a further understanding of the invention and constitute a part of this specification, illustrate embodiments of the invention and together with the description help to explain the principles of the invention. In the drawings.

DETAILED DESCRIPTION OF THE INVENTION

Reference will now be made in detail to the embodiments of the present invention, examples of which are illustrated in the accompanying drawings.

Figure 5:
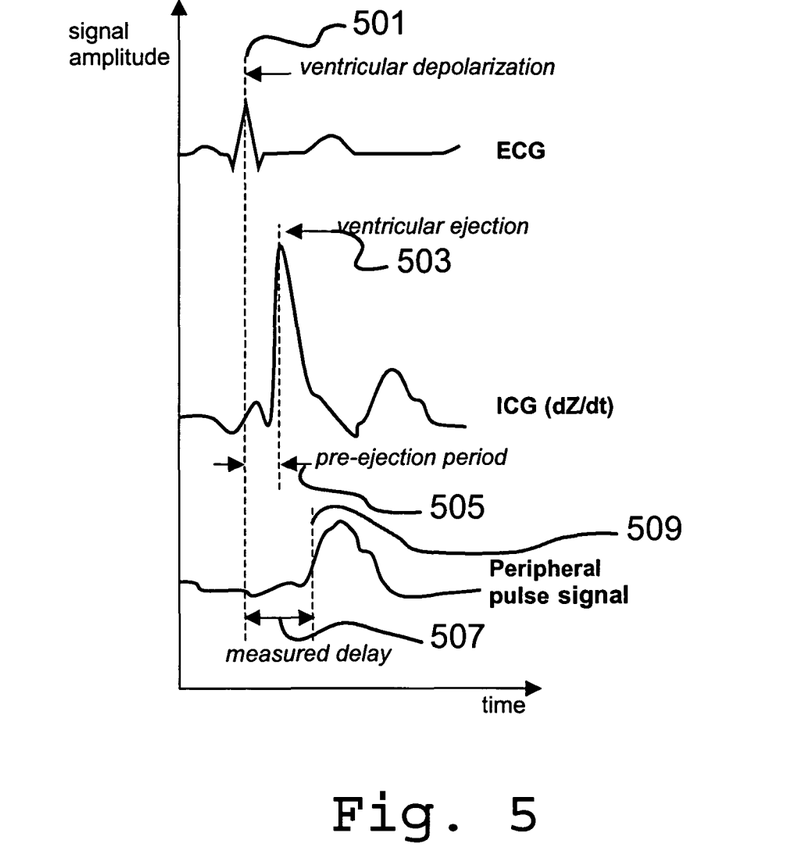
FIG. 5 shows the principle of the pulse wave transit time measurement

FIG. 5 shows a diagram showing the principle of the pulse wave transit time measurement. The ventricular depolarization time 501 is detected from the ECG signal. The ventricular ejection time 503 is most readily detected from a filtered and differentiated ICG signal. Between the ventricular depolarisation time 501 and the ventricular ejection time 503 is the pre-ejection period 505. Between the ventricular depolarisation time 501 and the beginning of the peripheral pulse peak 509 there is the measured delay 507.

Monitoring System

Figure 6A:
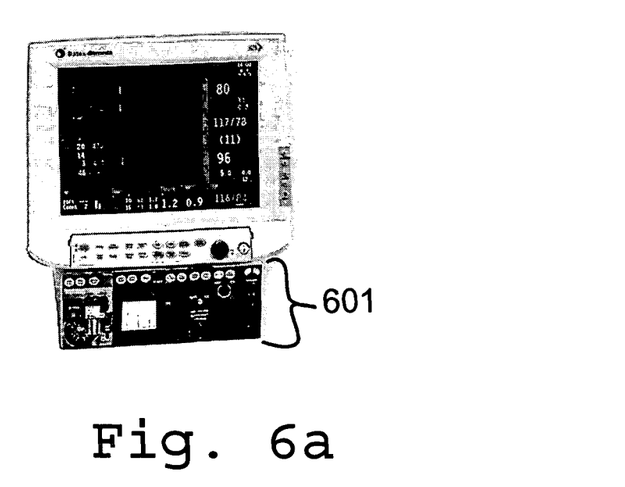
FIG. 6 shows Datex-Ohmeda S/5 anesthesia Monitor with the inventive parameter modules.

FIG. 6a shows Datex-Ohmeda S/5 Anesthesia Monitor. The parameter modules that accomplish the inventive method and system are located in the lower part 601 of the device.

The parameter modules are independent units with their own microprocessor. Their function is to collect and process physiological data. The monitor device serves as the user interface, displaying the data and allowing the user to customize the measurements. It also participates in data processing.

Figure 6B:
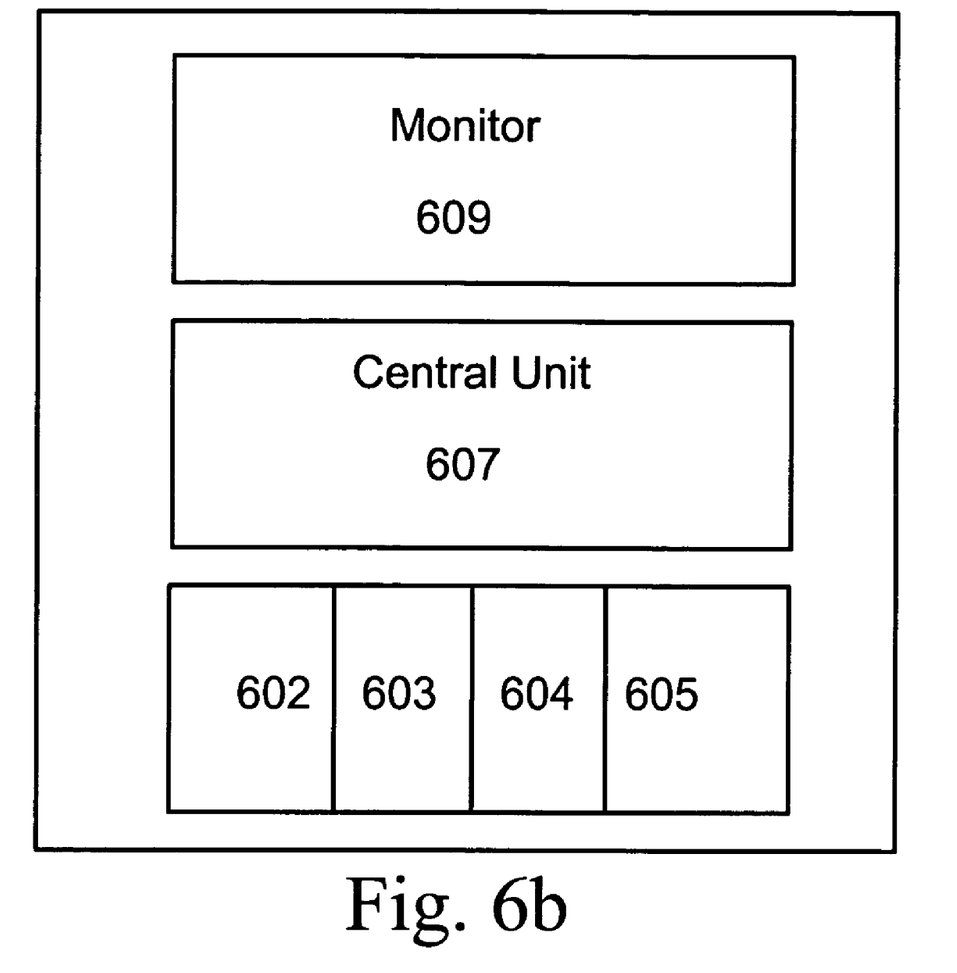

FIG. 6b shows a block diagram of the inventive system. The system comprises at least the following elements: An impedance cardiogram 602 for determining the mechanical heart beat starting time point of a patient, a peripheral site sensor (FIG. 4, 404) for determining the heart beat pulse arrival time at the peripheral site of the patient, a first calculator 604 for calculating the pulse wave transit time from the heart to the peripheral site by utilizing said mechanical starting point of the heart beat and said heart beat pulse arrival time at the peripheral site of the patient, a second calculator 605 for calculating the blood pressure of the patient from said pulse wave transit time. The system may also comprise a central unit 607 and a monitor 609.

The system for measuring non-invasively the blood pressure of a patient may also comprise an oscillometric cuff 404 for calibrating the blood pressure calculation by measuring the blood pressure of the patient.

In the system for measuring non-invasively the blood pressure of a patient the oscillometric cuff 404 may be adapted to perform the calibration of the blood pressure calculation by successive 1613 oscillometric cuff (FIG. 4, 404) measurements.

In the system for measuring non-invasively the blood pressure of a patient the calibration of the blood pressure calculation may be improved incrementally on each cuff 404 inflation cycle.

In the system for measuring non-invasively the blood pressure of a patient the peripheral site sensor 404 for determining the heart beat pulse arrival time at the peripheral site of the patient may be a plethysmographic sensor.

In the system for measuring non-invasively the blood pressure of a patient the plethysmographic sensor may be an optical reflectance means.

In the system for measuring non-invasively the blood pressure of a patient the peripheral site plethysmogram 404 may be arranged to correct a reflected wave component of the peripheral site plethysmogram 404 in response to a change in plethysmogram amplitude.

In the system for measuring non-invasively the blood pressure of a patient the system may be arranged to measure the beat to beat transit time start point by measuring the ECG QSR-complex, and the system may be arranged to add correction to the QRS-complex signal by averaging QRS to ICG waveform timing point.

Some of the preferable embodiments of the invention are depicted in the dependent patent claims.

Figure 7:
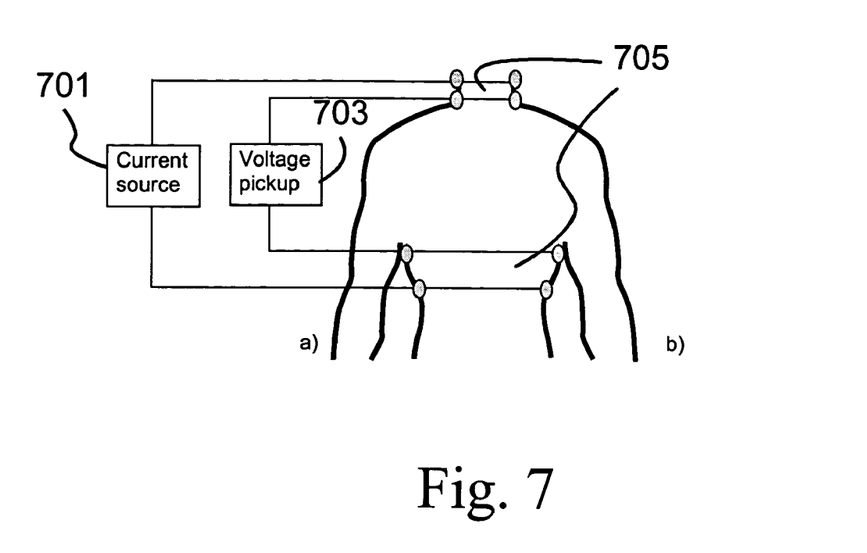
FIG. 7 shows electrode configurations used in impedance cardiography.

FIG. 7 shows electrode configurations used in impedance cardiography. Impedance cardiography i.e. (ICG) measurement is realized in the invention by modifying the impedance respiration (RESP) measurement, which determines the respiration rate from the respiratory component of the thoracic impedance signal. In the RESP measurement, low amplitude 62 kHz current is fed between two of the ECG electrode (FIG. 7), and the resulting voltage is measured with the same electrodes. The output is a large 62 kHz signal amplitude-modulated by a small $\Delta Z$-component including the respiratory and cardiac component. The signal is demodulated, then high pass filtered to remove the large DC component, and low pass filtered to limit the signal band to respiratory frequencies. For ICG measurement, the pass band of the filters was shifted to slightly higher frequencies, so that the respiratory component was removed along with the DC component, and the cardiac signal was accepted.

FIGS. 7, 8a, 8b and 8c further elaborate the impedance cardiogram (ICG). The impedance cardiogram is the recording of impedance changes in the thorax, associated with the pumping action of the heart. Feeding current (see FIG. 7, 701) into the tissue 705 and detecting consequential voltages 703 on the body surface measure the impedance cardiogram.

Figures 8A, 8B:
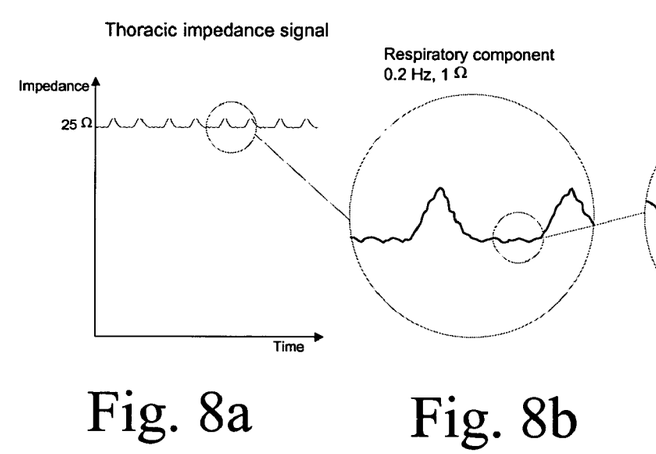
FIGS. 8a, 8b and 8c show the three components of the thoracic impedance signal.
Figure 8C:
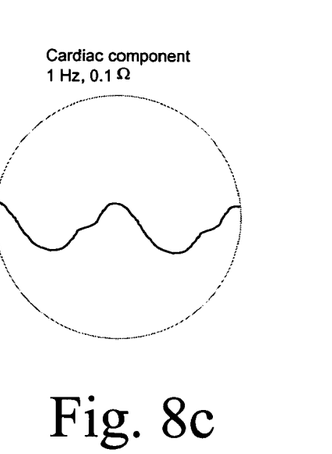

The thoracic impedance signal consists of three parts: the basal (FIG. 8a) impedance of the material between the electrodes, the impedance pneumogram (FIG. 8b) associated with respiration, and the impedance cardiogram associated with cardiac activity (FIG. 8c). As the cardiac impedance signal often is just 10% of the respiratory signal (see FIGS. 8b and 8c), some averaging is preferred, especially averaging synchronized to the heart beat, i.e. the QRS-complex signal that is depicted in FIG. 2.

Photoplethysmography

Plethysmograph is an instrument for determining variations in the volume of an organ or limb resulting from changes in the amount of blood in it. A plethysmographic trace from the wrist, for example, shows how the radial artery distends as a pressure pulse passes through it. The trace closely resembles an arterial pressure waveform.

Figure 4:
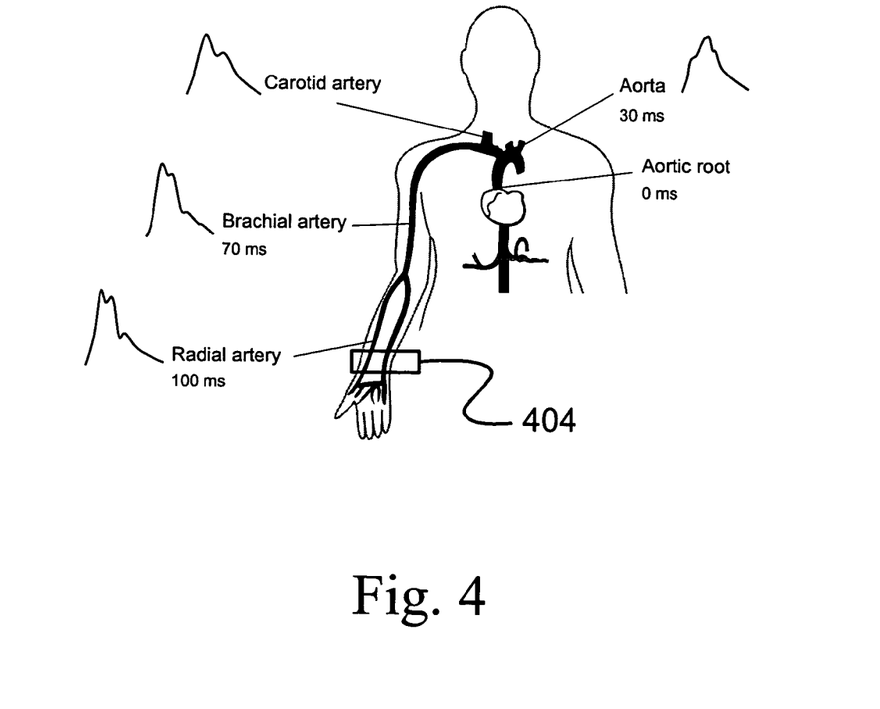
FIG. 4 shows aortic pressure pulses and their arrival times at different sites between the heart and the right arm.

FIG. 4 shows aortic pressure pulses and their arrival times at different sites between the heart and the right arm. Figure also shows a peripheral site sensor 404 for determining the heart beat pulse arrival time at the peripheral site of the patient. The peripheral site sensor 404 for determining the heart beat pulse arrival time at the peripheral site of the patient can be a plethysmographic sensor. Further the plethysmographic sensor 404 can be an optical reflectance means. In operation the peripheral site plethysmogram can be arranged to correct a reflected wave component of the peripheral site plethysmogram in response to a change in plethysmogram amplitude.

Three Essential Time Intervals

Three essential time intervals appear when elaborating this invention: dR-ICG, dR-pleth and dICG-pleth. They refer to measured or calculated values that may include contributions from e.g. signal processing. Corresponding physiological variables are summarized in Table 2. Changes in corresponding physiological and measured values are supposed to be equal, although absolute values may differ.

TABLE 2

Definitions of time intervals associated with the measurement.

| measured/ calculated time interval | $d_{R\text{-}ICG}$ | $d_{R\text{-}pleth}$ | $d_{ICG\text{-}pleth} = d_{R\text{-}pleth} - d_{R\text{-}ICG}$ |
|---|---|---|---|
| corresponding physiological time interval | delay between the ventricular depolarization and the onset of the aortic pulse wave = PEP | delay between the ventricular depolarization and the peripheral pulse | transit time of the pulse from the aortic root to the periphery |

Pulse Wave Transit Time Measurement

Figure 9:
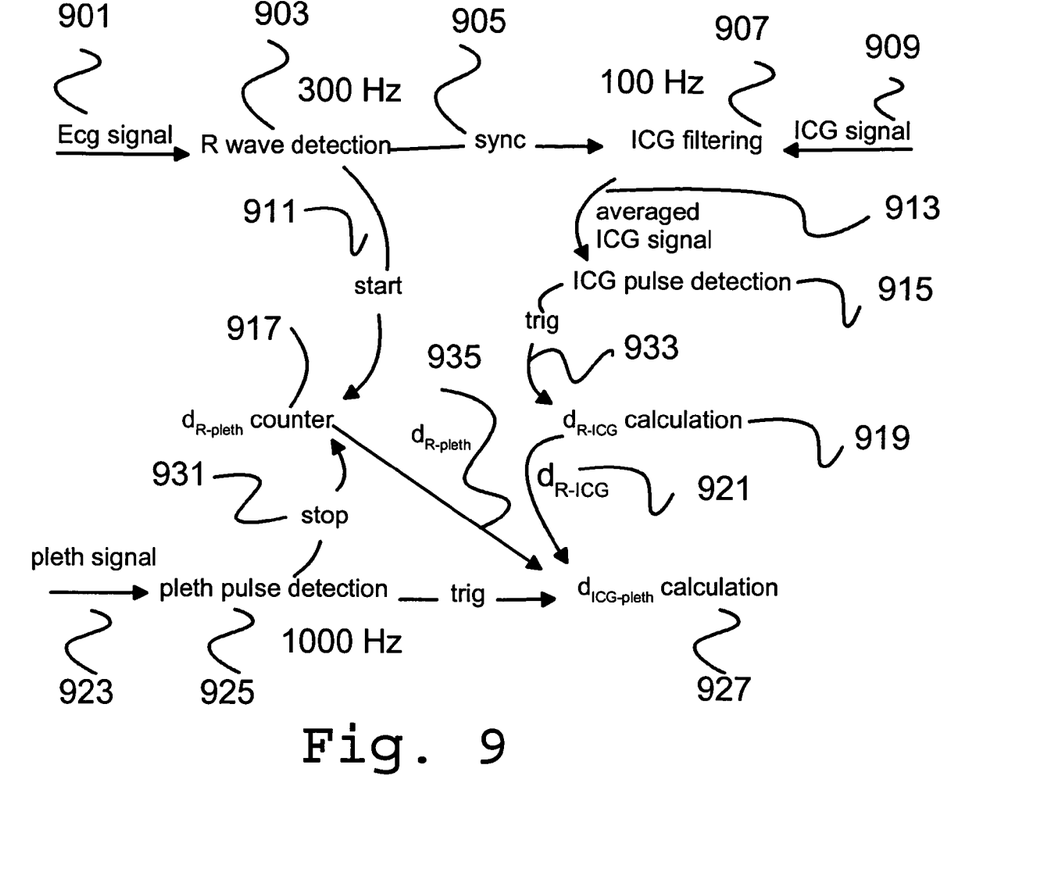
FIG. 9 shows a construction of the pulse wave transit time measurement software.

FIG. 9 shows the construction of the pulse wave transit time measurement software.

Pulse wave transit time measurement is implemented in the module software on the basis of an ECG/RESP software. The measurement consists of three main parts:

1) R wave detection 903 from the ECG
2) ICG signal processing 907 and pulse detection 915 and
3) plethysmogram pulse detection 923.

R wave detection 903 is implemented in the software as a 300 Hz interrupt function. Plethysmogram 923 and ICG handling 907, and pulse detection 915 are added in the 1000 Hz timer interrupt. FIG. 9 illustrates the interaction between these functions.

The R waves of the ECG 901 provide synchronization 905 for ICG filtering 907, and trigger 911 a 1000 Hz counter 917 to determine dR-pleth. The counter 917 will be stopped 931 when a plethysmogram pulse 923 will be detected 925. The ICG signal is filtered 907 by averaging 913 consecutive signal cycles sample by sample. A pulse detection 915 algorithm is applied on the averaged signal, and dR-ICG is determined 919 when a pulse is found. The delay dICG-pleth, which reflects the pulse wave transit time from the heart to the periphery, is calculated 927 as the difference of dR-ICG 921 and dR-pleth 935.

R Wave Triggered Operations

Figure 10:
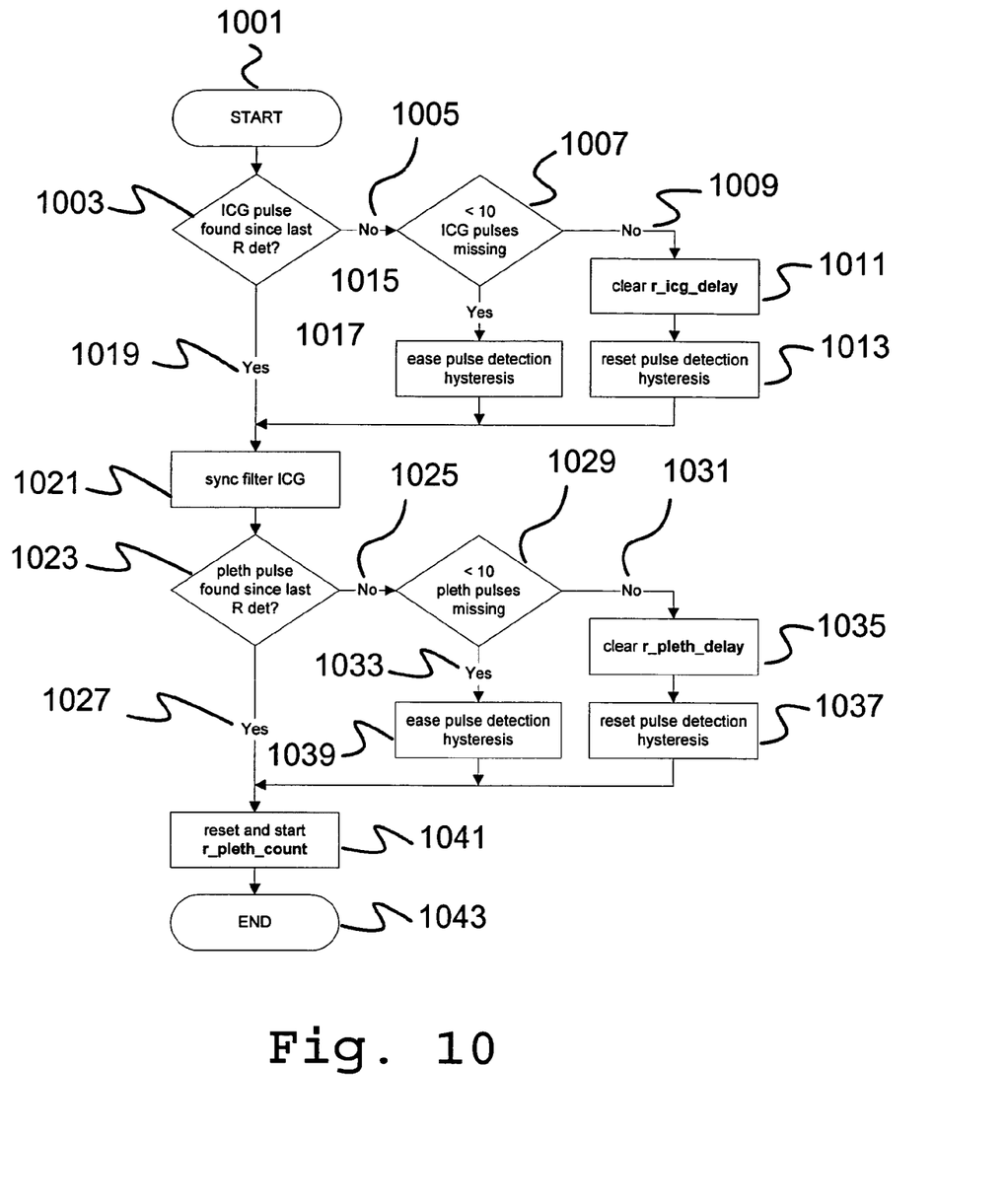
FIG. 10 shows a flowchart depicting the actions initiated by R wave detection.

FIG. 10 shows a flowchart that illustrates the actions performed immediately after R wave detection shown in FIG. 9, 903. The detection algorithm itself is described later in connection with FIG. 14. The main actions in FIG. 9 were in this respect the ICG filtering 907, and the starting 911 of the dR-pleth counter 917.

In the normal case, each R wave is followed by an ICG pulse and a plethysmogram pulse. Any missing pulse is noted, and pulse detection limits are eased to make sure that the next pulse will be found. If ten or more pulses are missing, the delay measurement is discontinued because there is no proper signal.

In FIG. 10 the operation starts at phase 1001. Then in step 1003 it is assessed if ICG pulse is found since last R wave detection. If yes 1019, then follows synchronization filter 1021. If there is no ICG pulse found 1005 it is assessed 1007 whether there is less than ten ICG pulses missing. If yes 1015, then pulse detection hysteresis is eased 1017, where after follows the synchronization filter ICG 1021. If no 1009, then the r_icg_delay is cleared 1011 and thus the number of ICG pulses missing is affected. After clearing the r_icg_delay the pulse detection hysteresis is reset 1013. Thereafter the operation progresses to step 1021. After the synchronization 1021 of the ICG filter it is assessed 1023 if the pleth pulse is found since last detection of R-signal. If yes, then the operation progresses to step 1041, where r_pleth_count-counter is reset and started. If no 1025, then it is again assessed 1029, whether less than 10 pleth pulses are missing. If yes 1033, then pulse detection hysteresis is eased 1039. Thereafter the operation progresses to step 1041, where r_pleth_count-counter is reset and started. If no 1031, then r_pleth_delay is cleared 1035 and pulse detection hysteresis is reset 1037. Thereafter the operation progresses also to step 1041, where r_pleth_count-counter is reset and started. After this the operation is ended 1043.

R Sync Filter For ICG

Figure 11A:
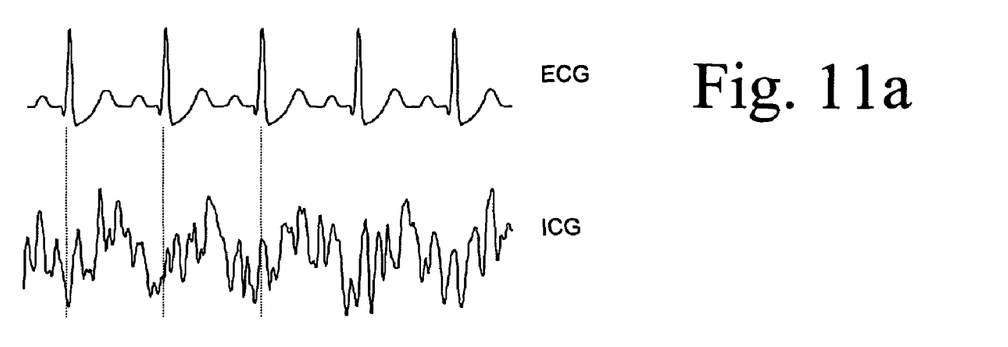
FIG. 11 shows the real time averaging of successive ICG pulses.
Figure 11B:
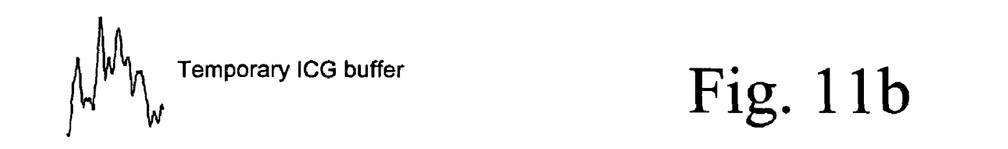
Figure 11C:
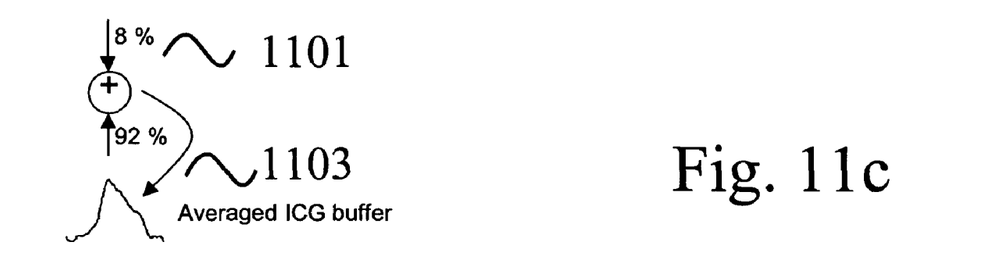

FIGS. 11a, 11b and 11c show real time averaging of successive ICG pulses. FIG. 11a illustrates the synchronization of the ICG signal by the R waves of the ECG, and the averaging of successive signal cycles. The procedure is based on two buffers, a temporary buffer FIG. 11b and an average buffer FIG. 11c, both having the same index which is increased each 10 ms. This index will be reset to zero at each R wave detection, so that both buffers contain one signal cycle starting from the same reference point. At 10 ms intervals, one new ICG sample will be stored into the temporary buffer FIG. 11b, and one sample will be read from the average buffer FIG. 11c for pulse detection and display.

Immediately after R detection, the contents of the two buffers are averaged with each other sample by sample, and the results will be stored back into the average buffer. The filtering procedure can be described mathematically as $$Y(i,nT) = wX(i,nT) + (1-w)Y(i-1,nT)$$

where Y and X are the averaged and raw signal, respectively, n is the sample index within each signal cycle, T is the sampling interval, i is the cycle index, and w is a weighting factor.

Figure 12:
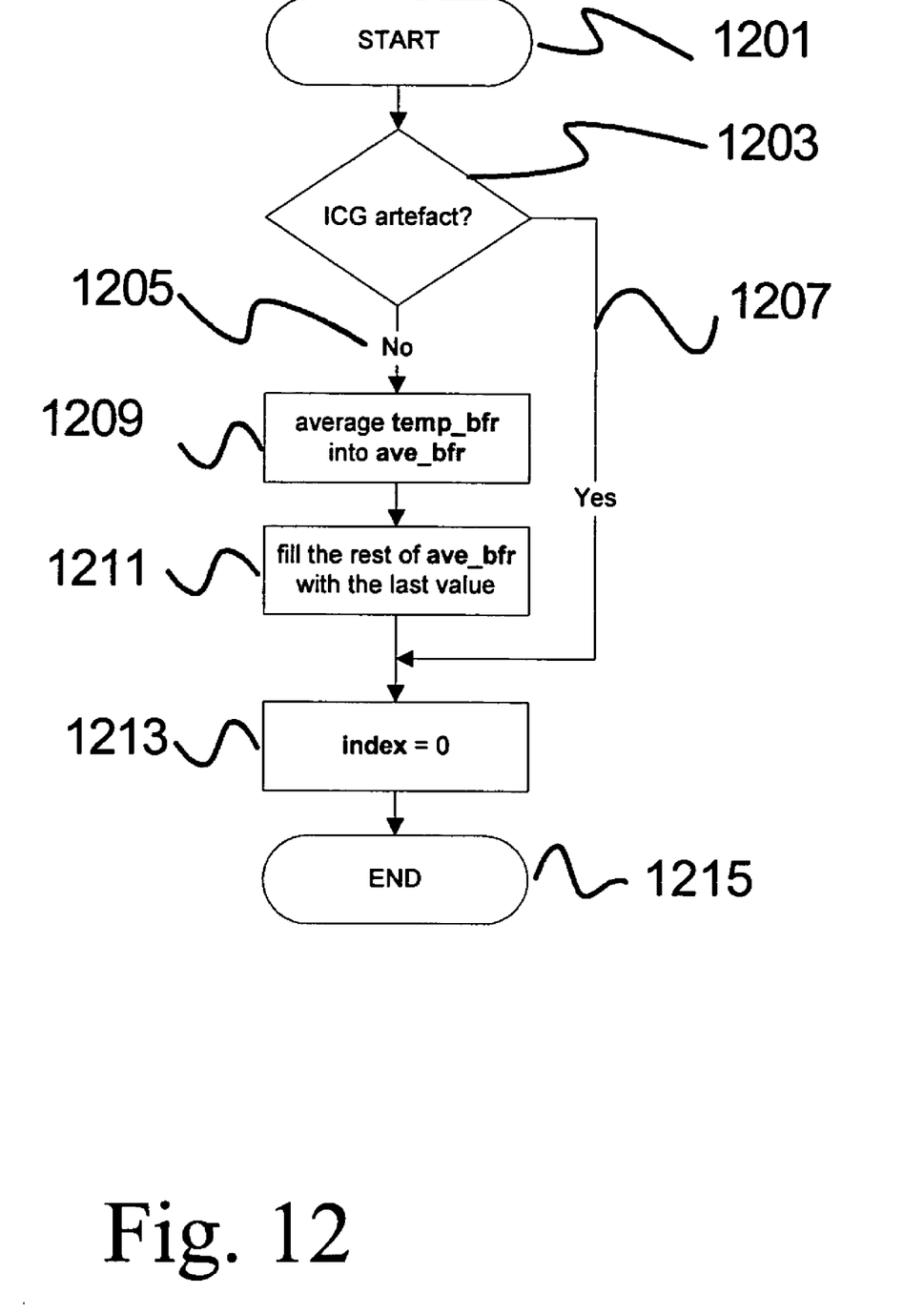
FIG. 12 shows a flowchart depicting the averaging of successive ICG signal cycles.

The flowchart in FIG. 12 describes the averaging function. More precisely FIG. 12 shows the averaging of successive ICG signal cycles. The method starts in step 1201. The averaging is performed only if the contents of the temporary buffer are free from artefacts. This is defined in step 1203. If there are no 1205 artefacts the temp_bfr is averaged into ave_bfr 1209. Otherwise, if there is ICG artefact 1207 the average buffer remains unchanged and the operation moves directly to step 1213. After step 1209 the ave_bfr is filled 1211 with the last value. Thus the tail of the average buffer is filled with the last newly averaged sample, so that it will not contain contributions from ancient signals in case that the beat interval increased again. Then, in both cases, the operation proceeds to step 1213 where the index is set to be zero. Thereafter the operation ceases 1215.

Figure 13:
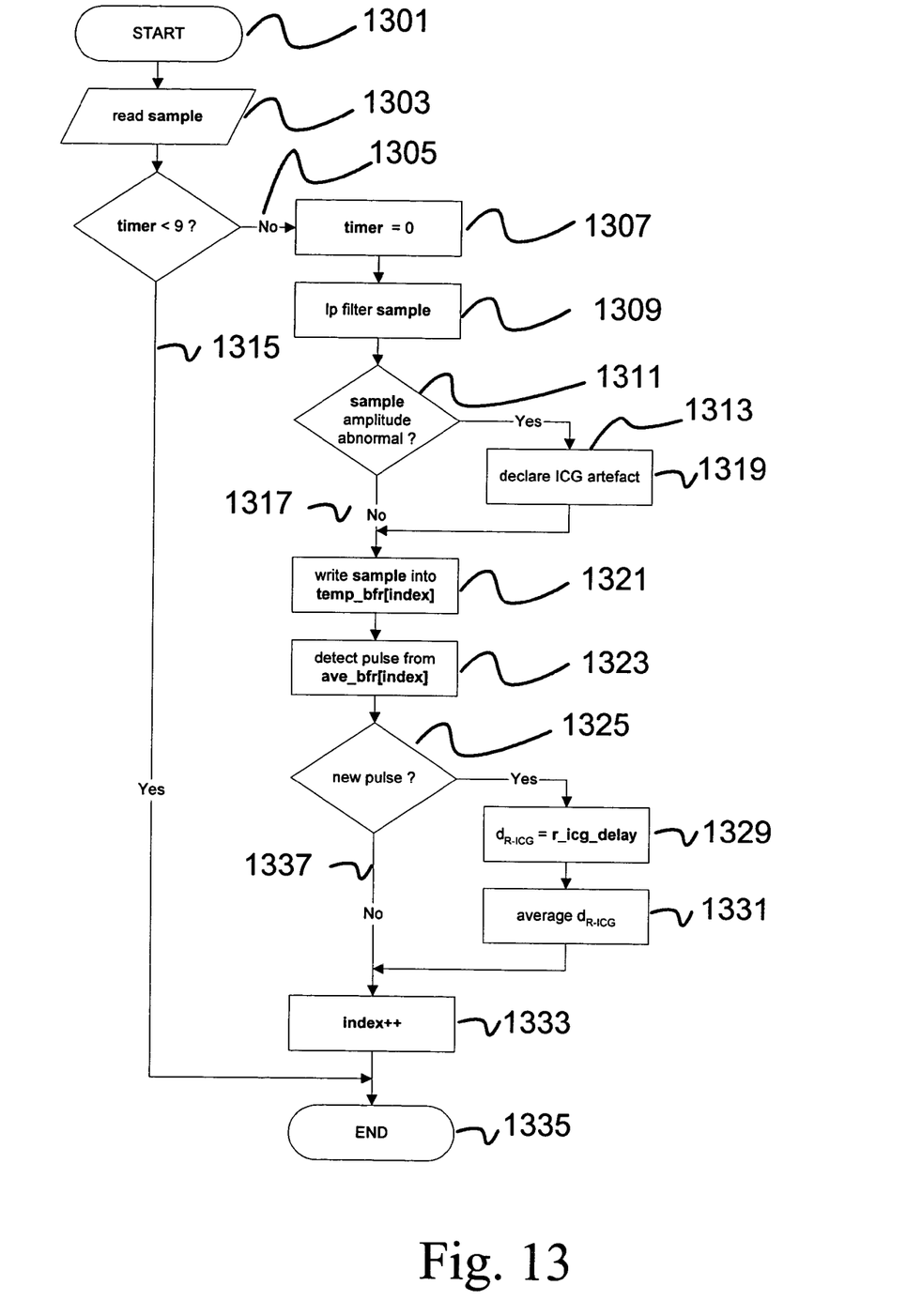
FIG. 13 shows a flowchart depicting the determination of dR-ICG

FIG. 13 shows determination of dR-ICG. The flowchart in FIG. 13 illustrates the filling of the temporary buffer and the determination of dR-ICG.

The process starts at 1301. Then ICG samples are read 1303 from the A/D converter e.g on each millisecond. Then the process implements a timer and a check 1304 for whether the timer is less than nine. If it is not 1305 less than nine, this means if the timer is more than nine, in this case ten, then the timer is set 1307 to be zero. After this the sample is low pass filtered 1309 and it is assessed 1311 whether the amplitude of the signal is abnormal. If the amplitude is abnormal 1313 then an ICG artefact is declared. After this, and also in the case that the amplitude is not abnormal 1317, i.e. in case the amplitude is normal, the sample is written 1321 into memory temp_bfr[index]. Then pulse is detected 1323 from ave_bfr[index]. After this it is decided whether a new pulse is assessed 1325. In a new pulse is assessed then it is set 1329 dR-ICG=r_icg_delay. After this the d R-ICG is averaged 1331. In case there is no new pulse 1337 or after step 1331 the index++ is added 1333 and thereafter the operation ceases 1335.

During the operation the samples are averaged to decrease the sampling frequency to 100 Hz. After the operation, the signal is then filtered with a FIR low pass filter. The filter has an additional notch at 50 Hz, so that any residual noise at mains frequency was removed.

Pulse Detection

Figure 14:
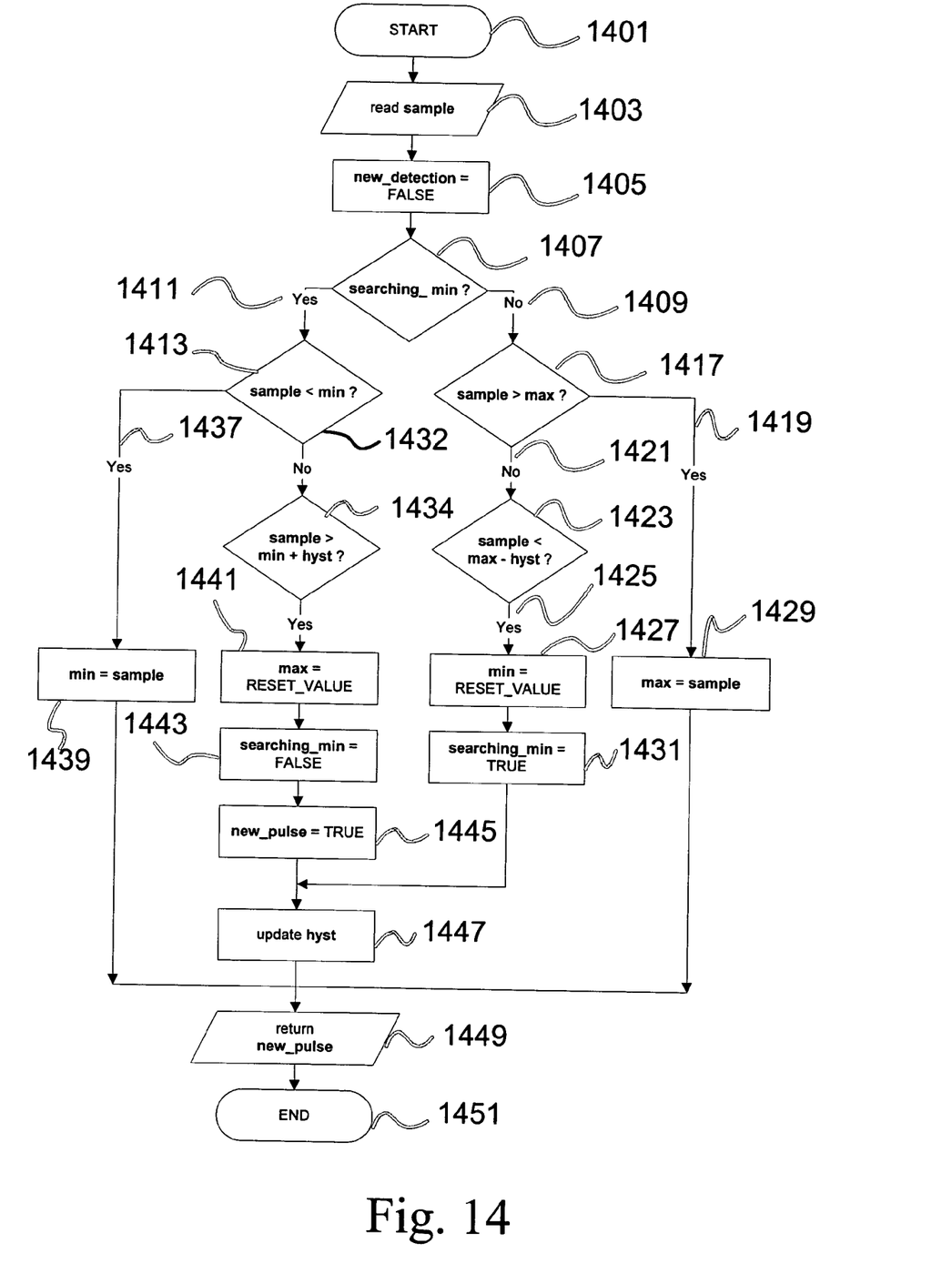
FIG. 14 shows a flowchart depicting the pulse detection algorithm for plethysmogram and ICG.

FIG. 14 shows pulse detection algorithm for plethysmogram and ICG. The flowchart in FIG. 14 describes the pulse detection algorithm. The same algorithm was used for both the ICG and the plethysmogram.

The operation of the algorithm is stated at step 1401. Then a sample is read 1403 and the new_detection-parameter is set 1405 to false. Thereafter it is assessed 1407 whether the minimum is searched. If yes 1411, then it is assessed 1413 whether the sample is lower than minimum. If yes, then the minimum is set 1439 to be the sample and thereafter the operation is returned 1449 to new pulse. If the sample is not 1432 lower than minimum then it is assessed 1434 whether the sample is higher than the minimum plus the hysteresis. If yes, then the maximum is set 1441 to reset_value. Thereafter, the searching_min is set 1443 to false. Thereafter the parameter new_pulse is set 1445 to be true. After this, the operation continues at step 1447 where the hysteresis is updated. Thereafter the operation continues in step 1449 by returning a new_pulse-parameter.

Likewise, if in step 1407 it is assessed 1407 that the minimum is not searched then the operation continues in step 1417, where it is assessed if the sample is higher than maximum. If it is 1419 the operation continues in step 1429, where the maximum is set to be the same as the sample. If in 1417 the sample is not 1421 higher than the maximum, then is assessed 1423 whether sample is higher than the maximum value  hysteresis. If yes, then the minimum is set 1427 to be the reset_value. Thereafter, the searching_min is set 1431 to true. After that the operation continues in step 1447, where the hysteresis is updated. Thereafter the operation continues at step 1449.

The algorithm determines the minimum and maximum value of each pulse. Maximum search is started when the signal has increased a degree of hysteresis above the minimum value. Correspondingly, minimum search is started when the signal has decreased a degree of hysteresis below the maximum value. A new pulse will be declared at the same point where the maximum search will be started, that is, on the rising edge of the pulse. Because the sharpest slope of the plethysmogram appears on the descending edge of the pulse, the signal will be reversed before applying the pulse detection algorithm.

Figure 15A:
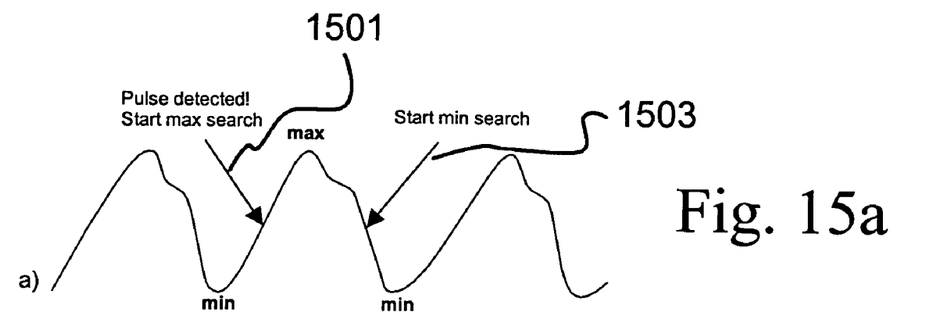
FIG. 15a shows the pulse detection and hysteresis levels for plethysmogram.
Figure 15B:
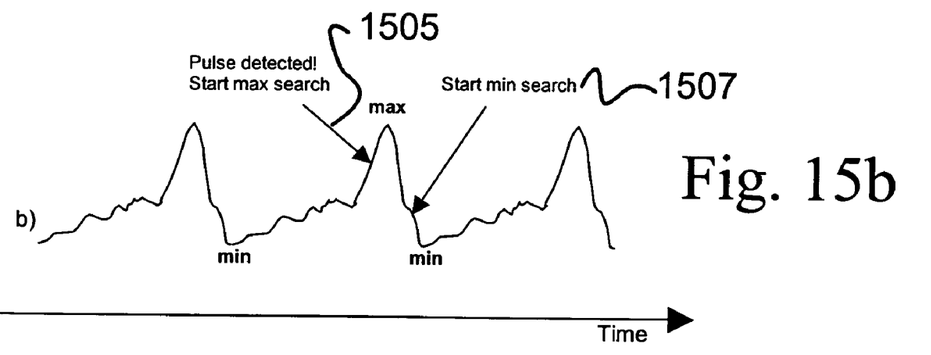
FIG. 15b shows pulse detection and hysteresis levels for ICG.

FIG. 15a shows pulse detection and hysteresis levels for plethysmogram. FIG. 15b shows pulse detection and hysteresis levels for ICG. In 1501 the pulse is detected and it is started to search for the pulse maximum. The maximum is founded in the peak of the signal. In 1503 it is started to search for the minimum of the signal. Later, the minimum of the graph and the level is found. The hysteresis value is repeatedly updated according to the pulse amplitude. The plethysmogram hysteresis value is adjusted towards half of the pulse amplitude. The shape of the ICG signal in FIG. 15b varies considerably depending on the patient and his/her position. To allow for wider peaks and smaller signal to noise ratio, the ICG hysteresis value (FIG. 15b) is set to two thirds of the pulse amplitude. Thus the pulse is detected in 1505, and maximum search is started. Later, in 1507 the minimum search is started. The effect of the hysteresis level is visualized in FIGS. 15a and 15b.

If the ICG signal is suddenly decreased to less than two thirds of its original size, the algorithm will not detect any pulses nor update the hysteresis. This is unlikely in a normal situation because the ICG signal is averaged and thus changed slowly. Movement of the patient, however, might cause sudden large signals in the ICG and in the plethysmogram alike. To handle such cases, the hysteresis is reduced if no pulses are detected. A minimum hysteresis level is defined to distinguish those situations in which there really is no pulsation.

Figure 16:
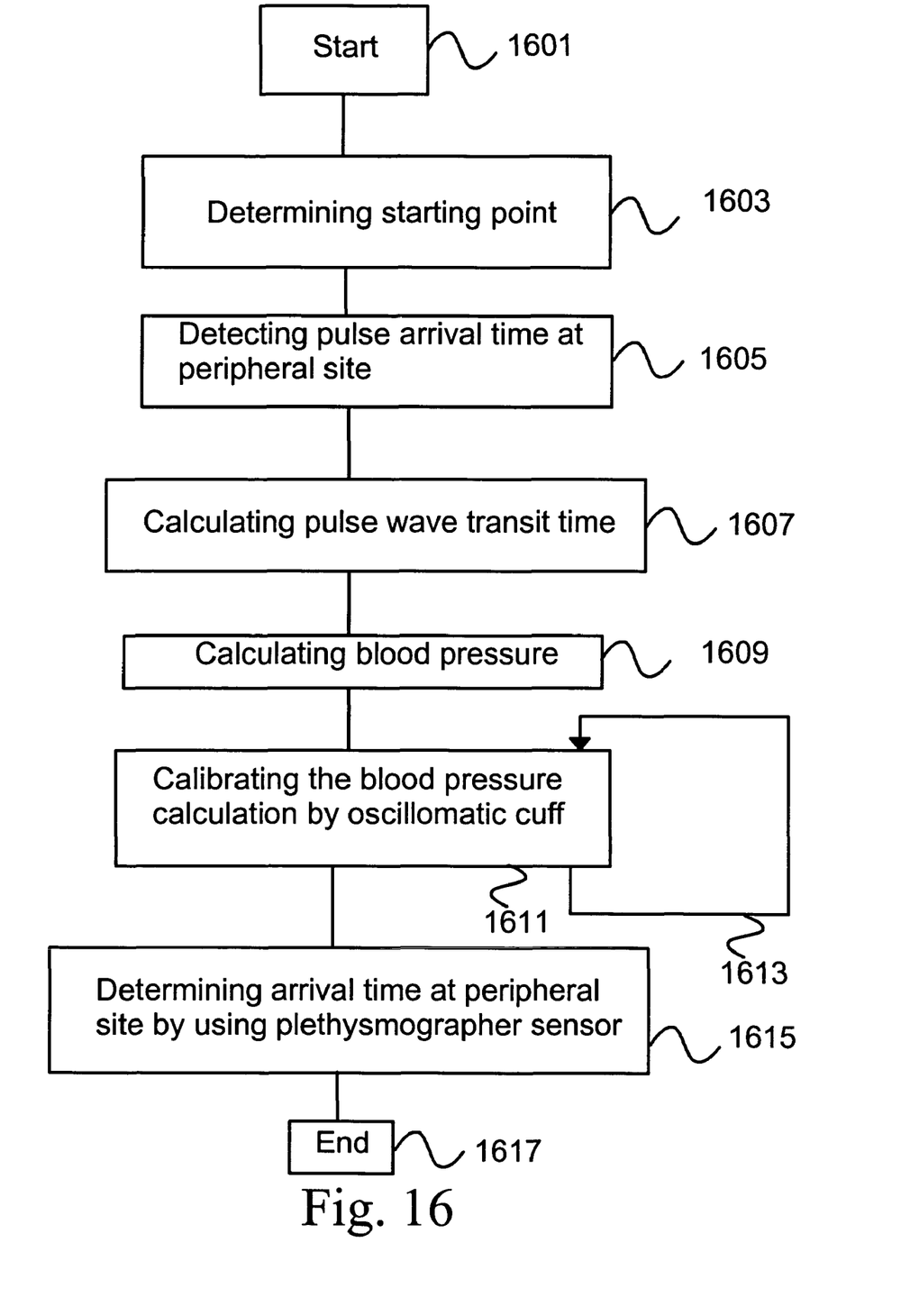
FIG. 16 shows a flowchart of the inventive method for measuring non-invasively a blood pressure of a patient.

FIG. 16 shows a flowchart of the inventive method for measuring non-invasively a blood pressure of a patient. The method comprises the following steps. The method begins with the start at 1601. Then follows the determining 1603 of a mechanical heart beat starting time point from an impedance cardiogram signal. After this follows the detecting 1605 of a heart beat pulse arrival time at a peripheral site of the patient. This peripheral site can be a wrist of the patient. Thereafter follows the calculating 1607 of a pulse wave transit time from the heart to the peripheral site by utilizing said mechanical starting point of the heart beat and said heart beat pulse arrival time, which were obtained in the steps of 1603 and 1605. Thereafter follows the calculating 1609 of an estimate of the blood pressure of the patient from said pulse wave transit time. This is the needed result of the calculations and a primary target of the invention.

In a second embodiment of the invention the method comprises also a step of calibrating 1611 the blood pressure calculation by oscillometric cuff 404 measurement of the blood pressure of the patient.

In a third embodiment of the invention the method comprises also a step of performing successively 1613 the previous step of calibrating 1611 the blood pressure calculation by oscillometric cuff 404 measurement.

In a fourth embodiment of the invention the step of calibrating the blood pressure calculation is improved incrementally on each cuff 404 inflation cycle 1613.

The fifth embodiment of the inventive method comprises the step of determining 1615 the heart beat pulse arrival time at the peripheral site of the patient by using peripheral site plethysmographic sensor 404.

The sixth embodiment of the inventive method comprises the step of measuring the peripheral site plethysmogram 404 with an optical reflectance means.

The sixth embodiment of the inventive method comprises the step of correcting a reflected wave component of the peripheral site plethysmogram 404 in response to a change in the plethysmogram amplitude.

The seventh embodiment of the inventive method comprises steps of measuring the heart beat to peripheral 404 pulse beat transit time start point by measuring the ECG QRS-complex, and adding correction to the QRS-complex signal by averaging QRS to ICG waveform timing point.

It is obvious to a person skilled in the art that with the advancement of technology, the basic idea of the invention may be implemented in various ways. The invention and its embodiments are thus not limited to the examples described above, instead they may vary within the scope of the claims.

The invention claimed is:

1. A method for measuring non-invasively a blood pressure of a patient,
   the method comprising the steps of:
   determining a mechanical heart beat starting time point from an impedance cardiogram signal,
   measuring the heart to peripheral site pulse beat transit time start point by measuring an ECG QRS-complex,
   adding correction to the ORS-complex signal by averaging a QRS to impedance cardiogram (ICE) waveform timing point,
   detecting a heart beat pulse arrival time at a peripheral site of the patient by using an optical plethysmographic sensor at the peripheral site,
   calculating a pulse wave transit time from the heart to the peripheral site by utilizing said mechanical starting point of the heart beat and said heart beat pulse arrival time,
   calculating an estimate of the blood pressure of the patient from said pulse wave transit time.

2. A method according to claim 1, wherein the method comprises a step of
   calibrating the blood pressure calculation by oscillometric cuff measurement of the blood pressure of the patient.

3. A method according to claim 2, wherein the method comprises the step of
   performing successively the step of calibrating the blood pressure calculation by oscillometric cuff measurement.

4. A method according to claim 3, wherein said step of calibrating the blood pressure calculation is improved incrementally on each cuff inflation cycle.

5. A method according to claim 1, wherein the method comprises a step of correcting a reflected wave component of a plethysmogram at the peripheral site in response to a change in the plethysmogram amplitude.

6. A system for measuring non-invasively the blood pressure of a patient wherein the system comprises:
   an impedance cardiogram for determining the mechanical heart beat starting time point of a patient,
   an optical plethysmographic sensor at a peripheral site for determining the heart beat pulse arrival time at the peripheral site of the patient,
   a first calculator for calculating the pulse wave transit time from the heart to the peripheral site by utilizing said mechanical starting point of the heart beat and said heart beat pulse arrival time at the peripheral site of the patient,
   a second calculator for calculating the blood pressure of the patient from said pulse wave transit times,
   said system further arranged to measure the pulse wave transit time start point by measuring an electrocardiogram (ECG) OSR-complex; and
   said system arranged to add correction to the QRS-complex signal by averaging QRS to impedance cardiogram (ICG) waveform timing point.

7. A system according to claim 6 for measuring non-invasively the blood pressure of a patient wherein said peripheral site plethysmogram is arranged to correct a reflected wave component of the plethysmogram at the peripheral site in response to a change in plethysmogram amplitude.

8. A system according to claim 6 for measuring non-invasively the blood pressure of a patient wherein the system comprises:
   an oscillometric cuff for calibrating the blood pressure calculation by measuring the blood pressure of the patient.

9. A system according to claim 8 for measuring non-invasively the blood pressure of a patient wherein the oscillometric cuff is adapted to perform the calibration of the blood pressure calculation by successive oscillometric cuff measurements.

10. A system according to claim 9 for measuring non-invasively the blood pressure of a patient wherein the calibration of the blood pressure calculation is improved incrementally on each cuff inflation cycle.

* * * * *